United States Patent [19]
Guillaumet et al.

[11] Patent Number: 6,057,317
[45] Date of Patent: May 2, 2000

[54] HETEROCYCLIC COMPOUNDS

[75] Inventors: Gérald Guillaumet, Saint Jean le Blanc; Jean-Yves Merour; Frédérique Touzeau, both of Olivet; Bruno Pfeiffer, Saint Leu la Foret; Pierre Renard, Versailles; Elisabeth Scalbert, Boulogne, all of France

[73] Assignee: Adir et Compagnie, Courbevoie, France

[21] Appl. No.: 09/119,423

[22] Filed: Jul. 20, 1998

[30]   Foreign Application Priority Data

Jul. 30, 1997 [FR] France .................................. 97 09709

[51] Int. Cl.[7] ........................ A61K 31/535; C07D 265/34
[52] U.S. Cl. ..................................... 514/230.2; 514/230.5; 514/314; 514/224.2; 544/56; 544/101; 544/105; 546/135
[58] Field of Search ............................. 544/56, 105, 101; 514/224.2, 230.5, 230.2, 314; 546/135

[56]   References Cited

PUBLICATIONS

Butler, R.C.M., et al., J. Heterocyclic Chem., 22, (1985) pp. 177–181.

*Primary Examiner*—Joseph McKane
*Attorney, Agent, or Firm*—The Firm of Gordon W. Hueschen

[57]   ABSTRACT

Compound of formula (I):

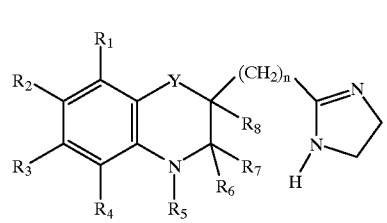

wherein:

Y, $R_1$, $R_2$, $R_3$, $R_4$, $R_5$, $R_6$, $R_7$, $R_8$ and n are as defined in the description, and medicinal products containing the same which are useful as imidazoline receptor ligands.

16 Claims, No Drawings

HETEROCYCLIC COMPOUNDS

The invention relates to new heterocyclic compounds. The new compounds are characterised structurally by the presence of an imidazoline nucleus substituted by a heterocyclic structure.

DESCRIPTION OF THE PRIOR ART

Some compounds of that type have been described in the literature for their $\alpha_2$-antagonist properties and for their usefulness in the treatment of depression (R. C. M. Butler et al., J. Heterocyclic Chem., 1985, 22, 177; EP 92328; EP 58006; EP 74711). The compounds of the present invention, on the other hand, have a very great affinity for imidazoline receptors, which is particularly valuable for the development of new pharmacologically active substances.

BACKGROUND OF THE INVENTION

There have recently been found in the central nervous system specific binding sites for compounds having an imidazoline structure (P. Bousquet et al., Biochem. Pharmacol., 1983, 32, 1459; J. Pharmacol. Exp. Ther., 1984, 230, 232), different from histamine receptors (P. Ernsberger et al. Soc. Neurosci. Abstr., 1986, 12, 1334). Those receptors have been characterised at the level of the nucleus reticularis lateralis, in the rotroventral portion of the medulla oblongata (G. Brica et al., Eur. J. Pharmacol., 1989, 162, 1), are distributed heterogeneously in the brain (P. Ernsberger et al., J. Pharmacol. Exp. Ther., 1990, 253, 408), and are also present at the peripheral level (P. Ernsberger et al., Am. J. Hypertens., 1990, 3, 90; J. E. Piletz et al., Biochem. Pharmacol., 1991, 42, 346). Two receptor sub-types, $I_1$ and $I_2$, have been identified (M. C. Michel et al., Trends Pharmacol. Sci., 1992, 13, 369) according to their ability to bind clonidine (sub-type $I_1$) and idazoxan (sub-type $I_2$).

Those receptors appear to be strongly implicated, together with $\alpha_2$-adrenoreceptors, in the vasodepressive and antihypertensive action of certain compounds such as clonidine and rilmenidine (G. Brica et al. Eur. J. Pharmacol., 1989, 162, 1; R. E. Gomez et al. Eur. J. Pharmacol., 1991, 195, 181). Their role in stimulating the release of insulin by the β cells of the pancreas has also been demonstrated (Schutz et al., Naunyn-Schniedeberg's Arch. Pharmacol., 1989, 340 (6/712). It has also been shown that imidazoline receptor ligands can be especially valuable in the treatment of psychiatric and neurological disorder (D. S. Nutt et al., Annals New York Academy of Sciences. 1995, 125). The compounds of the invention have a novel structure which surprisingly provides them with very great affinity for imidazoline receptors. They are thus able to be used in the treatment of pathologies associated with disturbances in the functioning of those receptors, such as cardio-vascular diseases and arterial hypertension, diabetes, obesity, and psychiatric and neurological disorders, such as depression, Parkinson's disease, anorexia, Alzheimer's disease, etc..

The compounds of the invention are especially useful in the treatment of cardiovascular diseases and arterial hypertension.

DETAILED DESCRIPTION OF THE INVENTION

More specifically, the present invention relates to compounds of formula (I):

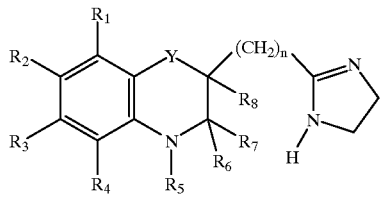

wherein:

n is 0 or 1,

Y represents an oxygen or sulphur atom or a $CH_2$ group, $R_1$, $R_2$, $R_3$ and $R_4$, which may be identical or different, each represent a hydrogen or halogen atom or a linear or branched ($C_1$–$C_6$)alkyl, ($C_3$–$C_7$)cycloalkyl, linear or branched ($C_1$–$C_6$)alkoxy, hydroxy, linear or branched ($C_1$–$C_6$) hydroxyalkyl, linear or branched ($C_1$–$C_6$) trihaloalkyl, linear or branched ($C_1$–$C_6$)alkyl-carbonyl, formyl, cyano, carboxy, linear or branched ($C_1$–$C_6$)alkoxy-carbonyl, nitro or optionally substituted amino group, or, ($R_1$–$R_2$) or ($R_2$–$R_3$) or ($R_3$–$R_4$) form with the carbon atoms bearing them an optionally substituted saturated or unsaturated 5- or 6-membered ring, $R_5$ represents a hydrogen atom, a ($C_3$–$C_7$)cycloalkyl group or a linear or branched ($C_1$–$C_6$)alkyl group optionally substituted by a group selected from ($C_3$–$C_7$)cycloalkyl and optionally substituted phenyl, or, with $R_4$, forms a saturated or unsaturated 5-, 6- or 7-membered ring optionally substituted by one or more identical or different groups selected from: linear or branched ($C_1$–$C_6$)alkyl, linear or branched ($C_1$–$C_6$)alkoxy, hydroxy, oxo, and optionally substituted amino, $R_6$ and $R_7$ each represent a hydrogen atom or together form an oxo group, $R_8$ represents a halogen or hydrogen atom or a linear or branched ($C_1$–$C_6$)alkyl, linear or branched ($C_1$–$C_6$) alkenyl, hydroxy, linear or branched ($C_1$–$C_6$)alkoxy (optionally substituted by an amino, pyrrolyl or piperidinyl group), ($C_3$–$C_7$)cycloalkyloxy, optionally substituted phenyloxy or optionally substituted benzyloxy group; or, with $R_7$, forms a bond.

with the proviso that:

when n is 0, Y represents an oxygen atom and each of $R_1$, $R_2$, $R_3$, $R_4$, $R_6$, $R_7$ and $R_8$ represents a hydrogen atom, then $R_5$ is other than a hydrogen atom or a methyl, ethyl or benzyl group, when n is 0, Y represents a sulphur atom and each of $R_1$, $R_2$, $R_3$, $R_4$, $R_6$, $R_7$ and $R_8$ represents a hydrogen atom, then $R_5$ is other than a hydrogen atom, their N-oxides, their enantiomers and diastereoisomers, and addition salts thereof with a pharmaceutically acceptable acid or base.

"Optionally substituted amino group" is understood to mean an amino group substituted by one or two groups, which may be identical or different, selected from linear or branched ($C_1$–$C_6$)alkyl, optionally substituted phenyl and optionally substituted benzyl.

The term "optionally substituted", applied to the groups phenyloxy, benzyloxy, phenyl and benzyl and also to the term "5- or 6-membered ring", means that those groups may be substituted by one or more substituents, identical or different, selected from halogen, linear or branched ($C_1$–$C_6$) alkyl, linear or branched ($C_1$–$C_6$)alkoxy, hydroxy and linear or branched ($C_1$–$C_6$)trihaloalkyl.

Amongst the pharmaceutically acceptable acids, there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid, etc..

Amongst the pharmaceutically acceptable bases, there may be mentioned by way of non-limiting example sodium hydroxide, potassium hydroxide, triethylamine, tert-butylamine, etc..

The invention relates especially to compounds of formula (I) wherein n is 0.

The preferred compounds of the invention are those wherein Y represents an oxygen atom. Other preferred compounds of the invention are those wherein Y represents a sulphur atom.

In the compounds of formula (I), preferably each of $R_6$, $R_7$ and $R_8$ represents a hydrogen atom.

In the compounds of formula (I), preferably three of the groups $R_1$, $R_2$, $R_3$ and $R_4$ are identical and each of the three presents a hydrogen atom, the remaining group being as defined in formula (I).

Other preferred compounds of formula (I) are those wherein ($R_1$–$R_2$) or ($R_2$–$R_3$) or ($R_3$–$R_4$) from with the carbon atoms bearing them an optionally substituted saturated or unsaturated 5- or 6-membered ring, for example a phenyl or cyclohexyl ring.

In the compounds of formula (I), a preferred group for $R_8$ is a linear or branched ($C_1$–$C_6$)alkyl group.

In the compounds of formula (I), a preferred group for $R_5$ is a linear or branched ($C_1$–$C_6$)alkyl group.

In the compounds of formula (I), especially, $R_4$, and $R_5$ together form an optionally substituted saturated or unsaturated 5-, 6- or 7-membered ring.

More especially, the invention relates to compounds of formula (I) wherein Y represents an oxygen atom, n is 0 each of $R_6$, $R_7$ and $R_8$ represents hydrogen atom, each of $R_1$, $R_2$, $R_3$ and $R_4$, which may be identical or different, represents a hydrogen or halogen atom or a linear or branched ($C_1$–$C_6$) alkyl, ($C_3$–$C_7$)cycloalkyl, linear or branched ($C_1$–$C_6$)alkoxy, hydroxy, linear or branched ($C_1$–$C_6$) hydroxyalkyl, linear or branched ($C_1$–$C_6$)trihaloalkyl, linear or branched ($C_1$–$C_6$) alkyl-carbonyl, formyl, cyano, carboxy, linear or branched ($C_1$–$C_6$)alkoxy-carbonyl, nitro or optionally substituted amino group, or, ($R_1$–$R_2$) or ($R_2$–$R_3$) or ($R_3$–$R_4$) form with the carbon atoms bearing them an optionally substituted saturated or unsaturated 5- or 6-membered ring, whilst $R_5$ represents a linear or branched ($C_1$–$C_6$)alkyl group or, with $R_4$, forms a saturated or unsaturated 5-6-or 7-membered ring.

The invention relates also to a process for the preparation of compounds of formula (I), characterised in that:

when, in the desired compound of formula (I), $R_4$ and $R_5$ do not together form a ring, there is used as starting material a compound of formula (II/a):

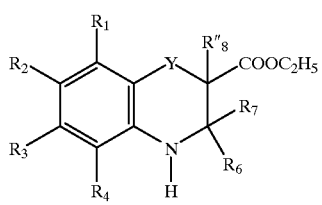

(II/a)

wherein R″$_8$ represents a hydrogen atom or, with $R_7$, forms a bond and Y, $R_1$, $R_2$, $R_3$, $R_4$, $R_6$ and $R_7$ are a defined for formula (I), which is treated with either:
a compound of formula (III):

R′$_5$—X        (III)

wherein X represents a halogen atom and R′$_5$ represents a ($C_3$–$C_7$)cycloalkyl group or a linear or branched ($C_1$–$C_6$)alkyl group optionally substituted by a ($C_3$–$C_7$)-cycloalkyl or optionally substituted phenyl group, to yield a compound of formula (II/b):

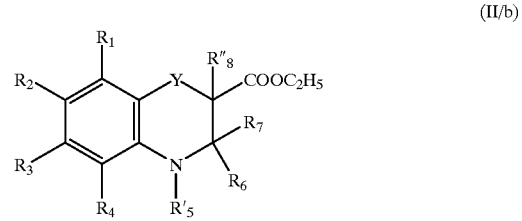

(II/b)

wherein Y, $R_1$, $R_2$, $R_3$, $R_4$, R′$_5$, $R_6$, $R_7$ and R″$_8$ are a defined above, which may, when R″$_8$ represents a hydrogen atom, be subjected to the action of a halogenating agent, or to the action of a strong base followed by treatment with a compound of formula (IV):

R′$_8$—X        (IV)

wherein X represents a halogen atom and R′$_8$, which is other than a hydrogen atom, has the same meaning as $R_8$ for formula (I), to yield a compound of formula (II/c):

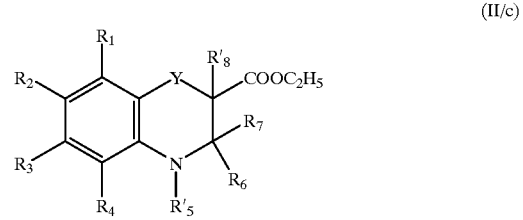

(II/c)

wherein Y, $R_1$, $R_2$, $R_3$, $R_4$, R′$_5$, $R_6$, $R_7$ and R′$_8$ are as defined above, or, when, in the compound of formula (II/a) used, R″$_8$ represents a hydrogen atom, with a compound of formula (IV) as defined above, after treatment with a strong base, to yield a compound of formula (II/d):

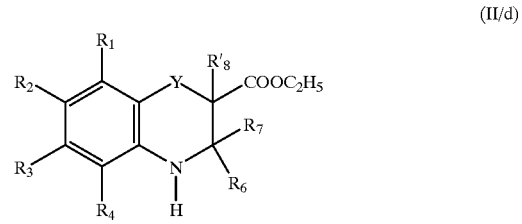

(II/d)

wherein Y, $R_1$, $R_2$, $R_3$, $R_4$, $R_6$, $R_7$ and R′$_8$ are as defined above, which compounds (II/a), (II/b), (II/c) and (II/d) constitute the totality of the compounds of formula (II):

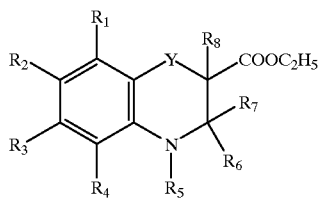
(II)

wherein Y, $R_1$, $R_2$, $R_3$, $R_4$, $R_5$, $R_6$, $R_7$ and $R_8$ are as defined above, which are treated, optionally after homologization of the chain that carries the ester function, with ethylenediamine to yield a compound of formula (I/a):

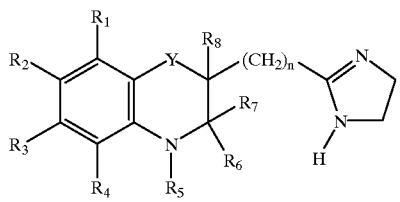
(I/a)

which is a particular case of the compounds of formula I wherein Y, $R_1$, $R_2$, $R_3$, $R_4$, $R_5$, $R_6$, $R_7$ $R_8$ and n have the same meanings as for formula (I), it being understood that $R_4$ and $R_5$ do not together form a ring, when, in the desired compound of formula (I), $R_4$ and $R_5$ together form a ring, there is used as starting material c compound of formula (II/e):

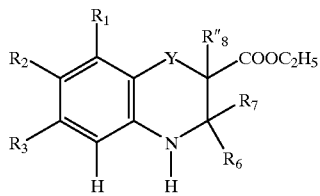
(II/e)

wherein $R_1$, $R_2$, $R_3$, $R_6$, $R_7$ and $R''_8$ are as defined above, which is treated with a compound of formula (V) or (VI):

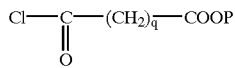
(V)

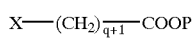
(VI)

wherein X represents a halogen atom or a leaving group, P represents a group that masks the acid function, and q is an integer 0, 1 or 2, to yield a compound of formula (VII):

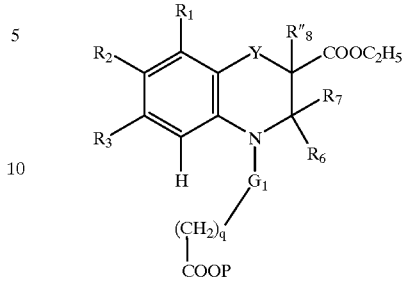
(VII)

wherein $G_1$ represents a $CH_2$ or CO group, and q, P, Y, $R_1$, $R_2$, $R_3$, $R_6$, $R_7$ and $R''_8$ have the same meanings as above, which, after freeing of the acid function and cyclisation, yields a compound of formula (VIII/a):

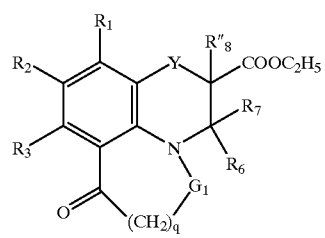
(VIII/a)

wherein Y, $R_1$, $R_2$, $R_3$, $R_6$, $R_7$, $R''_8$, $G_1$ and q have the same meanings as above, which compound (VIII/a), can be converted, after treatment with an alkyl halide, to a compound of formula (VIII/b)

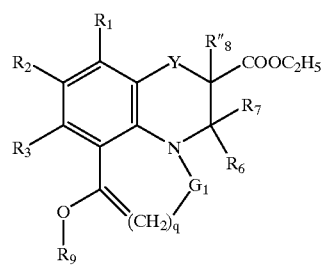
(VIII/b)

wherein $R_9$ represents a linear or branched $(C_1-C_6)$alkyl group, and Y, $R_1$, $R_2$, $R_3$, $R_6$, $R_7$, $R''_8$, $G_1$ and q have the same meanings as above, or can be reduced to yield a compound of formula (VIII/c):

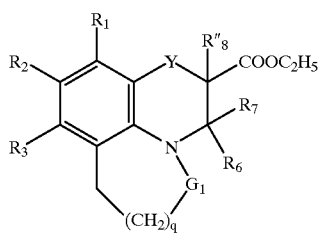
(VIII/c)

wherein Y, $R_1$, $R_2$, $R_3$, $R_6$, $R_7$, $R''_8$, $G_1$ and q are defined above, it being possible for each of the compounds (VIII/a), (VIII/b) and (VIII/c) to be treated, when that is compatible with the substituents present on the molecule, with a strong base and then with a compound of formula (IV) as defined above to yield a compound of formula (VIII/d):

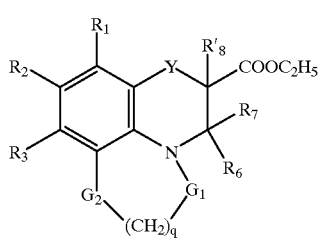
(VIII/d)

wherein $G_2$ represents a $CH_2$ or CO group or, with the carbon atom of the adjacent methylene, forms a group

and Y, $R_1$, $R_2$, $R_3$, $R_6$, $R_7$, $R'_8$, $G_1$ and q are as defined above, which compounds (VIII/a), (VIII/b), (VIII/c) and (VIII/d) constitute the totality of the compounds of formula (VIII):

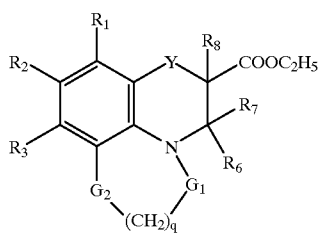
(VIII)

wherein $R_1$, $R_2$, $R_3$, $R_6$, $R_7$, $R_8$, $G_1$, $G_2$ and q are as defined above, and which are treated, optionally after homologization of the chain that carries the ester function, with ethylenediamine to yield a compound of formula (I/b):

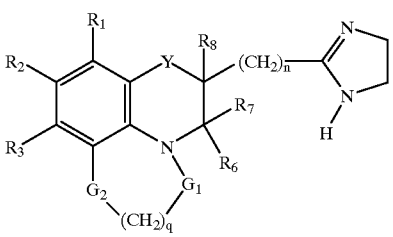
(I/b)

which is a particular case of the compounds of formula (I) wherein Y, $R_1$, $R_2$, $R_3$, $R_6$, $R_7$, $R_8$, $G_1$, $G_2$, n and q are as defined above, which compounds (I/a) and (I/b):
are optionally purified in accordance with a conventional purification technique,
optionally separated into their isomers in accordance with a conventional separation technique, and
converted, where appropriate, into their N-oxides or into addition salts thereof with a pharmaceutically acceptable acid or base.

In order to achieve a synthesis that is more appropriate to certain desired compounds of formula (I), it is possible to use a number of variants of the process indicated above.

One of those variants consists of using as starting material a compound of formula (IX):

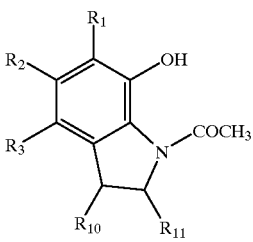
(IX)

wherein $R_{10}$ and $R_{11}$ simultaneously represent a hydrogen atom or together form a bond, and $R_1$, $R_2$ and $R_3$ have the same meanings as for formula (I), which, after deprotection of the indole nitrogen atom, is treated with ethyl 2,3-dibromopropionate in a basic medium to yield a compound of formula (X/a):

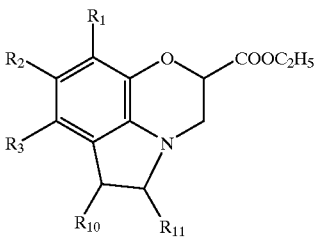
(X/a)

wherein $R_1$, $R_2$, $R_3$, $R_{10}$ and $R_{11}$ are as defined above,
which can be reacted with a strong base and with a compound of formula (IV):

$$R'_8—X \quad\quad (IV)$$

wherein X represents a halogen atom and R'$_8$, which is other than a hydrogen atom, has the same meaning as R$_8$ for formula (I), to yield a compound of formula (X/b):

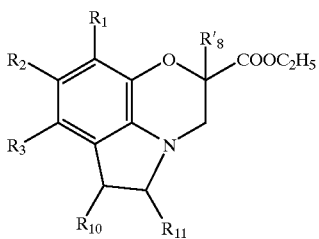

(X/b)

wherein R$_1$, R$_2$, R$_3$, R'$_8$, R$_{10}$ and R$_{11}$ are as defined above, which compounds (X/a) and (X/b) constitute the totality of the compounds of formula (X):

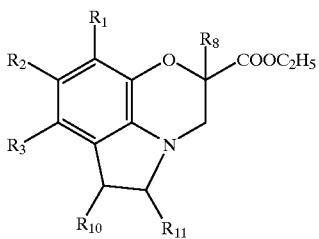

(X)

wherein R$_1$, R$_2$, R$_3$, R$_8$, R$_{10}$ and R$_{11}$ are defined as above, which are treated, after optional homologization of the chain that carries the ester function, with ethylenediamine to yield a compound of formula (I/c):

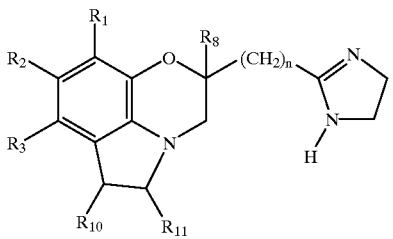

(I/c)

which is a particular case of the compounds of formula (I) wherein R$_1$, R$_2$, R$_3$, R$_8$, R$_{10}$, R$_{11}$ and n are as defined above, which compound (I/c):

is optionally purified in accordance with a conventional purification technique, optionally separated into its isomers in accordance with a conventional separation technique, and converted, where appropriate, into its N-oxide or into an addition salt thereof with a pharmaceutically acceptable acid or base, it being understood that when R$_{10}$ and R$_{11}$ each represent a hydrogen atom, they can be converted into a bond using a conventional technique of aromatization, at any stage of the process.

The invention relates also to pharmaceutical compositions comprising as active ingredient at least one compound of formula (I) on its own or in combination with one or more inert non-toxic excipients or carriers.

Amongst the pharmaceutical compositions according to the invention, there may be mentioned more especially those that are suitable for oral, parenteral or nasal administration, tablets or dragées, sublingual tablets, gelatin capsules, lozenges, suppositories, creams, ointments, dermal gels, etc..

The useful dosage varies according to the age and weight of the patient, the nature and severity of the affection and the mode of administration, which may be nasal, rectal, parenteral or oral. The unit dose generally ranges from 1 to 500 mg for treatment in from 1 to 3 administrations per 24 hours.

The following Preparations (Preparations A–D) yield synthesis intermediates for use in the preparation of the compounds of the invention.

Preparation A: 2-Ethoxycarbonyl-6-fluoro-2,3-dihydro-2H-1,4-benzoxazine

Step a: 4-Fluoro-2-aminophenol 47.7 mmol (10.8 g) of SnCl$_2$.H$_2$O are added to a solution of 7.96 mmol (1.26 g) of 4-fluoro-2-nitrophenol in 20 ml of ethanol. The solution is stirred at reflux for 2 hours. After cooling, the reaction mixture is hydrolysed over ice and rendered alkaline with a 30% sodium hydroxide solution. The mixture is extracted 4 times with ethyl acetate, and the combined organic phases are washed with an aqueous saturated sodium chloride solution and then dried over magnesium sulphate and concentrated to yield the expected product.

Step b: 2-Ethoxycarbonyl-6-fluoro-2,3-dihydro-2H-1,4-benzoxazine

The expected product is obtained in accordance with the process described in J.

Heterocyclic Chem., 1985, 22, 177, starting from the compound described in the preceding Step.

Preparation B: 2-Ethoxycarbonyl-6-trifluoromethyl-3,4-dihydro-2H-1,4-benzoxazine The expected product is obtained in accordance with the process described in Preparation A using 4-trifluoromethyl-2-nitrophenol as starting material.

Preparation C: 2-Ethoxycarbonyl-8-trifluoromethyl-3,4-dihydro-2H-1,4-benzoxazine The expected product is obtained in accordance with the process described in Preparation A using 6-trifluoromethyl-2-nitrophenol as starting material.

Preparation D: 2-Ethoxycarbonyl-7-methoxy-3,4-dihydro-2H-1,4-benzoxazine

The expected product is obtained in accordance with the process described in preparation A using 4-methoxy-2-nitrophenol as starting material.

The following Examples illustrate the invention but do not limit it in any way. The structures of the compounds described have been confirmed by the customary spectroscopic techniques.

EXAMPLE 1

2-(4,5-Dihydro-1H-2-imidazolyl)-4-propyl-3,4-dihydro-2H-1,4-benzoxazine oxalate

Step a: 2-Ethoxycarbonyl-4-propyl-2,3-dihydro-2H-1,4-benzoxazine 27.8 mmol (3.84 g) of potassium carbonate and 18.5 mmol (1.8 ml) of iodopropane are added to 9.2 mmol (1.92 g) of 2-ethoxycarbonyl-3,4-dihydro-2H-1,4-benzoxazine (described in J. Heterocyclic Chem., 1985, 22, 177) in 20 ml of acetonitrile and 2 ml of hexamethylphosphoramide. The reaction mixture is refluxed for 18 hours. After cooling and filtration, the filtrate is evaporated, taken up in a water/ethyl acetate mixture and extracted. The organic phase is dried, concentrated and purified by chromatography on silica gel using an ethyl acetate/petroleum ether mixture (1/9) as eluant to yield the expected compound.

Step b: 2-(4,5-Dihydro-1H-2-imidazolyl)-4-propyl-3,4-dihydro-2H1,4-benzoxazine

A solution of 18.8 mmol (1.13 g) of ethylenediamine in 50 ml of toluene is added to 18.8 mmol (9.4 ml) of 2M trimethylaluminium in toluene whilst maintaining the temperature at below 10° C. A solution of 11 mmol of the compound described in Step a in 10 ml of toluene is added, and the reaction mixture is refluxed for 3 hours. After cooling, a water/methanol/dichloromethane mixture (1/1/1) is added, and the mixture is then refluxed for a further 15 minutes. After cooling and filtration over Celite, the filtrate is concentrated. The residue is taken up in a water/dichloromethane mixture and extracted. The organic phase is dried, concentrated and purified by chromatography on silica gel using a dichloromethane/methanol/triethylamine mixture (98/2/1) as eluant to yield the title compound.

The corresponding oxalate is obtained by the action of a titrated solution of oxalic acid in ethanol.

Melting point (base): 138–140° C.

Elemental microanalysis:

|  | C | H | N |
|---|---|---|---|
| % calculated | 57.29 | 6.32 | 12.53 |
| % found | 57.39 | 6.33 | 12.39 |

EXAMPLE 2

2-(4,5-Dihydro-1H-2-imidazolyl)-4,6-dimethyl-3,4-dihydro-2H-1,4-benzoxazine oxalate Step a: 2-Ethoxycarbonyl-4,6-dimethyl-3,4-dihydro-2H-1,4-benzoxazine The expected product is obtained in accordance with the process described in Example 1, Step a, replacing iodopropane by iodomethane and using 2-ethoxycarbonyl-6-methyl-3,4-dihydro-2H-1,4-benzoxazine (prepared in accordance with the process described in J. Heterocyclic Chem., 1985, 22, 177, starting from 2-hydroxy-5-methylaniline) as starting material.

Step b: 2-(4,5-Dihydro-1H-2-imidazolyl)-4,6-dimethyl-3,4-dihydro-2H-1,4-benzoxazine Oxalate The expected product is obtained in accordance with the process described in Example 1, Step b, starting from the compound described in the preceding Step.

Elemental microanalysis:

|  | C | H | N |
|---|---|---|---|
| % calculated | 56.07 | 5.96 | 13.08 |
| % found | 55.86 | 5.89 | 12.80 |

EXAMPLE 3

2-(4,5-Dihydro-1H-2-imidiazolyl)-4,5-dimethyl-3,4-dihydro-2H-1,4-benzoxazine Oxalate Step a: 4,5-Dimethyl-2-ethoxycarbonyl-3,4-dihydro-2H-1,4-benzoxazine The expected product is obtained in accordance with the process described in Example 1, Step a, replacing iodopropane by iodomethane and using 2-ethoxycarbonyl-5-methyl-3,4-dihydro-2H-1,4-benzoxazine (prepared in accordance with the process described in J. Heterocyclic Chem., 1985, 22, 177, starting from 2-hydroxy-4-methylaniline) as starting material.

Step b: 2-(4,5-Dihydro-1H-2-imidazolyl)-4,5-dimethyl-3,4-dihydro-2H-1,4-benzoxazine Oxalate The expected product is obtained in accordance with the process described in Example 1, Step b, starting from the compound described in the preceding Step.

Melting point (base): 132–134° C.

Elemental microanalysis:

|  | C | H | N |
|---|---|---|---|
| % calculated | 56.07 | 5.96 | 13.08 |
| % found | 56.07 | 5.98 | 12.98 |

EXAMPLE 4

6-Chloro-2-(4,5-dihydro-1H-2-imidazolyl)-4-methyl-3,4-dihydro-2H-1,4-benzoxazine Oxalate Step a: 6-Chloro-2-ethoxycarbonyl-4-methyl-2H-1,4-benzoxazine The expected product is obtained in accordance with the process described in Example 1, Step a, replacing iodopropane by iodomethane and using 6-chloro-2-ethoxycarbonyl-3,4-dihydro-2H-1,4-benzoxazine (prepared in accordance with the process described in J. Heterocyclic Chem., 1985, 22, 177, starting from 2-hydroxy-4-chloroaniline) as starting material.

Step b: 6-Chloro-2-(4,5-dihydro-1H-2-imidazolyl)-4-methyl-3,4-dihydro-2H-1,4-benzoxazine Oxalate The expected product is obtained in accordance with the process described in Example 1, Step b, starting from the compound described in the preceding Step.

Melting point (base): 170–172° C.

Elemental microanalysis:

|  | C | H | N |
|---|---|---|---|
| % calculated | 49.20 | 4.72 | 12.30 |
| % found | 49.17 | 4.70 | 12.27 |

EXAMPLE 5

2-(4,5-Dihydro-1H-2-imidazolyl)-2,4-dimethyl-3,4-dihydro-2H-1,4-benzoxazine Oxalate Step a: 2,4-Dimethyl-2-methoxycarbonyl-3,4-dihydro-2H-1,4-benzoxazine 20 ml of 5% KOH are added to 11.3 mmol (2.5 g) of 2-ethoxycarbonyl-4-methyl-3,4-dihydro-2H-1,4-benzoxazine (described in J. Heterocyclic Chem., 1985, 22, 177) in 10 ml of ethanol and 10 ml of tetrahydrofuran. The reaction mixture is stirred at room temperature for 1 hour. The solvent is evaporated off, and the resulting residue is taken up in an ethyl acetate/water mixture, at acidic pH, and extracted. The organic phase is dried and concentrated. The residue is then dissolved in 90 ml of tetrahydrofuran and the temperature is reduced to −50° C. before the addition of 45.2 mmol (22.6 ml) of lithium diisopropylamide as a 2M solution in tetrahydrofuran. The reaction mixture is stirred for 2 hours at −50° C., and then 45.2 mmol (2.7 ml) of iodomethane are added and the temperature is brought back up to 25° C. in the course of 2 hours. After hydrolysis, the mixture is acidified to pH=4 and extracted with ethyl acetate. The organic phase is dried and concentrated. The residue is then dissolved in 150 ml of methanol in the presence of para-toluenesulphonic acid. The reaction mixture is heated at reflux for 18 hours. The solvent is evaporated off, and the mixture is taken up in an ethyl acetate/water mixture and extracted. The organic phase is dried, concentrated and purified by chromatography on silica gel using an ethyl acetate/petroleum ether mixture (3/7) as eluant to yield the expected compound.

Step b: 2-(4,5-Dihydro-1H-2-imidazolyl)-2,4-dimethyl-3,4-dihydro-2H-1,4-benzoxazine Oxalate The expected product is obtained in accordance with the process described in Example 1, Step b, starting from the compound described in the preceding Step.

Elemental microanalysis:

|  | C | H | N |
|---|---|---|---|
| % calculated | 56.07 | 5.96 | 13.08 |
| % found | 56.40 | 6.10 | 12.55 |

EXAMPLE 6

2-(4,5-Dihydro-1H-2-imidazolyl)-4-methyl-2-propyl-3,4-dihydro-2H-1,4-benzoxazine Oxalate Step a: 2-Methoxycarbonyl-4-methyl-2-propyl-3,4-dihydro-2H-1,4-benzoxazine The expected product is obtained in accordance with the process described in Example 5, Step a, replacing iodomethane by 1-iodopropane.

Step b: 2-(4,5-Dihydro-1H-2-imidazolyl)-4-methyl-2-propyl-3,4-dihydro-2H-1,4-benzoxazine Oxalate The expected product is obtained in accordance with the process described in Example 1, Step b, starting from the compound obtained in the preceding Step.

Elemental microanalysis:

|  | C | H | N |
|---|---|---|---|
| % calculated | 58.44 | 6.63 | 12.03 |
| % found | 58.67 | 6.79 | 12.01 |

EXAMPLE 7

2-(4,5-Dihydro-1H-2-imidazolyl)-2,4-dimethyl-3,4-dihydro-2H-1,4-benzoxazin-3-one Step a: 2,4-Dimethyl-2-ethoxycarbonyl-3,4-dihydro-2H-1,4-benzoxazin-3-one 5.5 mmol (1.2 g) of 2-ethoxycarbonyl-3,4-dihydro-2H-1,4-benzoxazin-3-one (described in C.R. Acad. Sci. Paris Series C, 1969, 269, 154) in 5 ml of dimethylformamide are added at 0° C. to a suspension of 11 mmol (0.44 g) of 60% sodium hydride in 5 ml of dimethyformamide. The reaction mixture is stirred at 0° C. for 30 minutes. 22.2 mmol (1.38 ml) of iodomethane are then added, and the reaction mixture is stirred at room temperature for 1 hour. After hydrolysis and extraction with ethyl acetate, the organic phase is dried, concentrated and purified by chromatography on silica gel using an ethyl acetate/petroleum ether mixture (3/7) as eluant to yield the expected compound.

Step b: 2-(4,5-Dihydro-1H-2-imidazolyl)-2,4-dimethyl-3,4-dihydro-2H-1,4-benzoxazin-3-one The expected product is obtained in accordance with the process described in Example 1, Step b, starting from the compound obtained in the preceding Step, and stopping at the state of the free base.

Melting point: 152–154° C.

Elemental microanalysis:

|  | C | H | N |
|---|---|---|---|
| % calculated | 63.65 | 6.18 | 17.13 |
| % found | 63.55 | 6.20 | 17.51 |

EXAMPLE 8

2-(4,5-Dihydro-1H-2-imidazolyl)-2,3,6,7-tetrahydro-5H[1,4]oxazino-[2,3,4-i,j]quinoline Oxalate

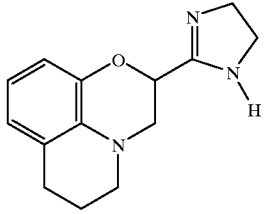

Step a: 4-[2-(Benzyloxycarbonyl)-ethyl]-2-ethoxycarbonyl-3,4-dihydro-2H-1,4-benzoxazine 2.3 mmol (0.9 ml) of 40% Triton B in water are added at 0° C. to 22.6 mmol (5 g) of 2-ethoxycarbonyl-3,4-dihydro-2H-1,4-benzoxazine (described in J. Heterocyclic Chem., 1985, 22, 177) and 79 mmol (12.8 g) of benzyl acrylate in 17 ml of toluene. The reaction mixture is refluxed overnight, the solvent is evaporated off and the reaction mixture is heated again for 24 hours. After cooling, hydrolysis and extraction with ethyl acetate, the organic phase is concentrated and purified by chromatography on silica gel using an ethyl acetate/petroleum ether mixture (3/7) as eluant to yield the expected compound.

Step b: 2-Ethoxycarbonyl-7-oxo-2,3,6,7-tetrahydro-5H[1,4]oxazino[2,3,4-i,j]-quinoline 0.15 g of 10% palladium-on-carbon is added to 4 mmol (1.5 g) of the compound obtained in the preceding Step in 20 ml of ethanol. The reaction mixture is stirred under a hydrogen atmosphere for 4 hours, the catalyst is then filtered off and the filtrate is concentrated. Trifluoroacetic anhydride (8 mmol) is added at 0° C. to the resulting residue dissolved in 10 ml of dichloromethane. The reaction mixture is stirred at room temperature for 5 hours and then hydrolysed. The reaction mixture is adjusted to basic pH using 5N sodium hydroxide solution, and the mixture is extracted with ethyl acetate. The organic phase is concentrated and purified by chromatography on silica gel using dichloromethane as eluant to yield the expected compound.

Step c: 2-Ethoxycarbonyl-2,3,6,7-tetrahydro-5H[1,4]oxazino[2,3,4-i,j]quinoline 50 mg of 10% palladium-on-carbon are added to 0.76 mmol (0.2 g) of the compound described in the preceding Step in 20 ml of ethanol. The reaction mixture is stirred under a hydrogen atmosphere for 48 hours. The catalyst is filtered off, and the filtrate is concentrated and purified by chromatography on silica gel using dichloromethane as eluant to yield the expected compound.

Step d: 2-(4,5-Dihydro-1H-2-imidazolyl)-2,3,6,7-tetrahydro-5H[1,4]oxazino[2,3,4-i,j]quinoline Oxalate The expected product is obtained in accordance with the process described in Example 1, Step b, starting from the compound described in the preceding Step.

Elemental microanalysis:

|  | C | H | N |
|---|---|---|---|
| % calculated | 57.65 | 5.74 | 12.61 |
| % found | 57.10 | 5.77 | 12.28 |

EXAMPLE 9

2-(4,5-Dihydro-1H-2-imidazolyl)-8-methyl-2,3,6,7-tetrahydro-5H[1,4]-oxazino[2,3,4-i,j]quinoline Oxalate

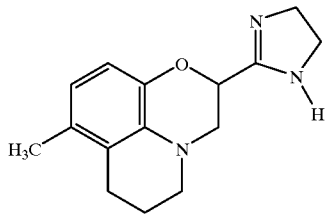

Step a: 4-[2(Benzyloxycarbonyl)-ethyl]-2-ethoxycarbonyl-6-methyl-3,4-dihydro2H-1,4-benzoxazine The expected product is obtained in accordance with the process described in Example 8, Step a, starting from 2-ethoxycarbonyl-6-methyl-3,4-dihydro-2H-1,4-benzoxazine.

Step b: 2-Ethoxycarbonyl-8-methyl-7-oxo-2,3,6,7-tetrahydro-5H[1,4]oxazino-[2,3,4-i,j]quinoline The expected product is obtained in accordance with the process described in Example 8, Step b, starting from the compound described in the preceding Step.

Step c: 2-(4,5-Dihydro-1H-2-imidazolyl)-8-methyl-2,3,6,7-tetrahydro-5H[1,4]-oxazino[2,3,4-i,j]quinoline Oxalate The expected product is obtained in accordance with the process described in Example 1, Step b, starting from the compound described in the preceding Step.

Elemental microanalysis:

|  | C | H | N |
|---|---|---|---|
| % calculated | 58.78 | 6.09 | 12.10 |
| % found | 58.50 | 6.11 | 11.92 |

EXAMPLE 10

2-(4,5-Dihydro-1H-2-imidazolyl)-7-hydroxy-2,3-dihydro-5H[1,4]oxazino-[2,3,4-i,j]quinolin-5-one

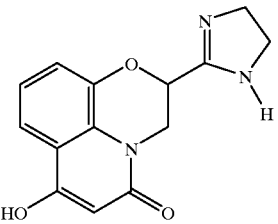

Step a: 4-[2-(Benzyloxycarbonyl)-acetyl]-2-ethoxycarbonyl-3,4-dihydro-2H-1,4-benzoxazine 54.6 mmol (7.6 ml) of triethylamine and 35.9 mmol (7.64 g) of benzyl 3-chloro-3-oxopropanoate are added to 17.1 mmol (3.53 g) of 2-ethoxycarbonyl-3,4-dihydro-2H-1,4-benzoxazine (described in J. Heterocyclic Chem., 1985, 22, 177) in 35 ml of dichloromethane. The reaction mixture is stirred at room temperature for 1 hour. After hydrolysis and extraction with dichloromethane, the organic phase is concentrated and purified by chromatography on silica gel using an ethyl acetate/petroleum ether mixture (2/8) as eluant to yield the expected compound.

Step b: 2-Ethoxycarbonyl-7-hydroxy-2,3-dihydro-5H[1,4]oxazino[2,3,4-i,j]-quinolin-5-one The expected product is obtained in accordance with the process described in Example 8, Step b, starting from the compound described in the preceding Step.

Step c: 2-(4,5-Dihydro-1H-2-imidazolyl)-7-hydroxy-2,3-dihydro-5H[1,4]oxazino-[2,3,4-i,j]quinolin-5-one The expected product is obtained in accordance with the process described in Example 1, Step b, starting from the compound described in the preceding Step, stopping at the stage of the free base.

EXAMPLE 11

2-(4,5-Dihydro-1H-2-imidazolyl)-7-hydroxy-8-methyl-2,3-dihydro-5H-[1,4]oxazino[2,3,4-i,j]quinolin-5-one

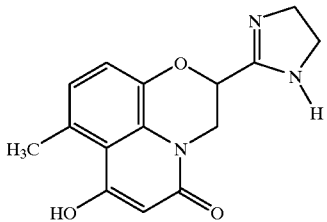

Step a: 4-[2-(Benzyloxycarbonyl)-acetyl]-2-ethoxycarbonyl-6-methyl-3,4-dihydro-2H-1,4-benzoxazine The expected product is obtained in accordance with the process described in Example 10, Step a, using 2-ethoxycarbonyl-6-methyl-3,4-dihydro-2H-1,4-benzoxazine as starting material.

Step b: 2-Ethoxycarbonyl-7-hydroxy-8-methyl-2,3-dihydro-5H[1,4]oxazino[2,3,4-i,j]quinolin-5-one The expected product is obtained in accordance with the process described in Example 8, Step b, starting from the compound described in the preceding Step.

Step c: 2-(4,5-Dihydro-1H-2-imidazolyl)-7-hydroxy-8-methyl-2,3-dihydro-5H[1,4]-oxazino[2,3,4-i,j]quinolin-5-one The expected product is obtained in accordance with the process described in Example 1, Step b, starting from the compound described in the preceding Step, stopping at the stage of the free base.

EXAMPLE 12

2-(4,5-Dihydro-1H-2-imidazolyl)-7-methoxy-2,3-dihydro-5H[1,4]oxazino-[2,3,4-i,j]quinolin-5-one

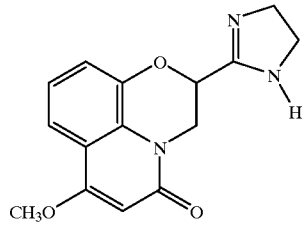

Step a: 2-Ethoxycarbonyl-7-methoxy-2,3-dihydro-5H[1,4]oxazino[2,3,4-i,j]-quinolin-5-one 7.3 mmol (1 g) of potassium carbonate and 5.4 mmol (1 g) of methyl tosylate are added to 3.6 mmol (1 g) of the compound described in Example 10, Step b, in 10 ml of dimethylformamide. The reaction mixture is heated at 50° C. for 1 hour and then hydrolysed and extracted with ethyl acetate. The organic phase is concentrated and purified by chromatography on silica gel using dichloromethane as eluant to yield the expected compound.

Step b: 2-(4,5-Dihydro-1H-2-imidazolyl)-7-methoxy-2,3-dihydro-5H[1,4]oxazino-[2,3,4-i,j]quinolin-5-one The expected product is obtained in accordance with the process described in Example 1, Step b, starting from the compound described in the preceding Step, stopping at the stage of the free base.

Melting point: 228–230° C.

Elemental microanalysis:

|  | C | H | N |
|---|---|---|---|
| % calculated | 63.15 | 5.30 | 14.73 |
| % found | 62.49 | 5.39 | 14.07 |

EXAMPLE 13

2-(4,5-Dihydro-1H-2-imidazolyl)-7-methoxy-8-methyl-2,3-dihydro-5H-[1,4]oxazino[2,3,4-i,j]quinolin-5-one

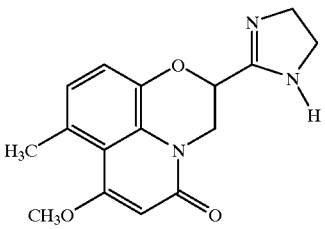

Step a: 2-Ethoxycarbonyl-7-methoxy-8-methyl-2,3-dihydro-5H[1,4]oxazino[2,3,4-i,j]quinolin-5-one The expected product is obtained in accordance with the process described in Example 12, Step a, starting from the compound described in Example 11, Step b.

Step b: 2-(4,5-Dihydro-1H-2-imidazolyl)-7-methoxy-8-methyl-2,3-dihydro-5H[1,4]-oxazino[2,3,4-i,j]quinolin-5-one The expected product is obtained in accordance with the process described in Example 1, Step b, starting from the compound described in the preceding Step, stopping at the stage of the free base.

Melting point: 222–224° C.

Elemental microanalysis:

|  | C | H | N |
|---|---|---|---|
| % calculated | 64.20 | 5.72 | 14.04 |
| % found | 64.02 | 5.87 | 13.36 |

EXAMPLE 14

2-(4,5-Dihydro-1H-2-imidazolyl)-1,2,7,8,9,10-hexahydro-10a-aza-3-oxa-cyclohepta[d,e]naphthalene Oxalate

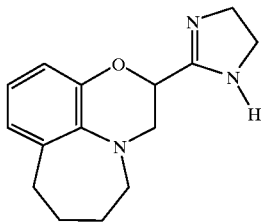

Step a: 4-[3-(Benzyloxycarbonyl)-propionyl]-2-ethoxycarbonyl-3,4-dihydro-2H-1,4-benzoxazine The expected product is obtained in accordance with the process described in Example 10, Step a, replacing benzyl 3-chloro-3-oxopropanoate by benzyl 4-chloro-4-oxobutanoate.

Step b: 4-[3-(Benzyloxycarbonyl)-propyl]-2-ethoxycarbonyl-3,4-dihydro-2H-1,4-benzoxazine 32.5 mmol (32.5 ml) of BH$_3$. THF (1M solution in tetrahydrofuran) are added to 10.8 mmol (4.3 g) of the compound described in Step a in 20 ml of tetrahydrofuran. The reaction mixture is heated at reflux for 4 hours. After cooling and removal of the solvent by evaporation, the residue is taken up in a water/ethyl acetate mixture and extracted. The organic phase is dried, concentrated and purified by chromatography on silica gel using an ethyl acetate/petroleum ether mixture (3/7) as eluant to yield the expected compound.

Step c: 2-Ethoxycarbonyl-7-oxo-1,2,7,8,9,10-hexahydro-3-oxa-10a-azacyclohepta[d,e]-naphthalene The expected product is obtained in accordance with the process described in Example 8, Step b, starting from the compound described in the preceding Step.

Step d: 2-Ethoxycarbonyl-1,2,7,8,9,10-hexahydro-3-oxa-10a-azacyclohepta[d,e]-naphthalene The expected product is obtained in accordance with the process described in Example 8, Step c, starting from the compound described in the preceding Step.

Step e: 2-(4,5-Dihydro-1H-2-imidazolyl)-1,2,7,8,9,10-hexahydro-3-oxa-10a-azacyclohepta[d,e]naphthalene Oxalate The expected product is obtained in accordance with the process described in Example 1, Step b, starting from the compound described in the preceding Step.

Elemental microanalysis:

|  | C | H | N |
|---|---|---|---|
| % calculated | 58.77 | 6.11 | 12.10 |
| % found | 58.67 | 6.12 | 11.87 |

EXAMPLE 15

2-(4,5-Dihydro-1H-2-imidazolyl)-2,3,5,6-tetrahydro[1,4]oxazino[2,3,4-h,i]indole Oxalate

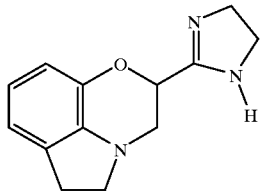

Step a: 7-Hydroxyindoline

The expected product was obtained in accordance with the process described in J. Chem. Soc. (c), 1966, 344.

Step b: 2-Ethoxycarbonyl-2,3,5,6-tetrahydro[1,4]oxazino[2,3,4-h,i]indole 0.85 mmol (0.12 ml) of ethyl 2,3-dibromopropionate is added to a solution of 0.8 mmol (0.1 g) of the compound described in the preceding Step, in 2 ml of acetone, in the presence of 2.1 mmol (0.3 g) of potassium carbonate. The reaction medium is heated at reflux for 18 hours. After cooling and filtration, the solvent is evaporated off. The residue is taken up in a water/ethyl acetate mixture and extracted. The organic phase is dried and purified by chromatography on silica gel using an ethyl acetate/petroleum ether mixture (1/9) as eluant to yield the expected compound.

Step c: 2-(4,5-Dihydro-1H-2-imidazolyl)-2,3,5,6-tetrahydro[1,4]oxazino[2,3,4-h,i]-indole Oxalate The expected product is obtained in accordance with the process described in Example 1, Step b, starting from the compound described in the preceding Step.

Elemental microanalysis:

|  | C | H | N |
|---|---|---|---|
| % calculated | 56.42 | 5.37 | 13.16 |
| % found | 56.24 | 5.42 | 12.96 |

EXAMPLE 16

2-(4,5-Dihydro-1H-2-imidazolyl)-2,3-dihydro[1,4]oxazino[2,3,4-h,i]indole Oxalate

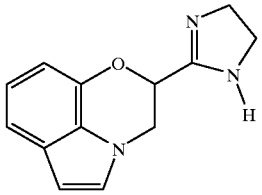

Step a: 2-Ethoxycarbonyl-2,3-dihydro[1,4]oxazino[2,3,4-h,i]indole 0.90 mmol (0.204 g) of DDQ is added at 0° C. to a solution of 0.86 mmol (0.2 g) of the compound described in Example 15, Step b, in 6 ml of toluene. The reaction mixture is stirred at that temperature for 30 minutes before being hydrolysed. After neutralisation with a 5% sodium hydroxide solution and extraction with ethyl acetate, the combined organic phases are dried over magnesium sulphate and concentrated. Purification by chromatography on silica gel using an ethyl acetate/petroleum ether mixture (1/9) as eluant enables the expected product to be isolated.

Step b: 2-(4,5-Dihydro-1H-2-imidazolyl)-2,3-dihydro[1,4]oxazino[2,3,4-h,i]indole Oxalate The expected product is obtained in accordance with the process described in Example 1, Step b, starting from the compound described in the preceding Step.

Melting point: 190–192° C.

EXAMPLE 17

2-(4,5-Dihydro-1H-2-imidazolyl)-4,7-dimethyl-3,4-dihydro-2H-1,4-benzoxazine Oxalate Step a: 2-Ethoxycarbonyl-4,7-dimethyl-3,4-dihydro-2H-1,4-benzoxazine The expected product is obtained in accordance with the process described in Example 1, Step a, replacing iodopropane by iodomethane and using 2-ethoxycarbonyl-7-methyl-3,4-dihydro-2H-1,4-benzoxazine (prepared in accordance with the method described in J. Heterocyclic Chem., 1985, 22, 177, starting from 2-amino-5-methylphenol) as starting material.

Step b: 2-(4,5-Dihydro-1H-2-imidazolyl)-4,7-dimethyl-3,4-dihydro-2H-1,4-benzoxazine Oxalate The expected product is obtained in accordance with the process described in Example 1, Step b, using the compound described in the preceding Step as starting material.

Melting point (base): 106–108° C.

EXAMPLE 18

2-(4,5-Dihydro-1H-2-imidazolyl)-4,8-dimethyl-3,4-dihydro-2H-1,4-benzoxazine Oxalate

Step a: 2-Ethoxycarbonyl-4,8-dimethyl-3,4-dihydro-2H-1,4-benzoxazine

The expected product is obtained in accordance with the process described in Example 1, Step a, replacing iodopropane by iodomethane and using as starting material 2-ethoxycarbonyl-8-methyl-2,3-dihydro-2H-1,4benzoxazine, prepared in accordance with the method described in J. Heterocyclic Chem., 1985, 22, 177, starting from 2-amino-6-methylphenol (described in J. Org. Chem., 1996, 3289).

Step b: 2-(4,5-Dihydro-1H-2-imidazolyl)-4,8-dimethyl-3,4-dihydro-2H-1,4-benzoxazine Oxalate The expected product is obtained in accordance with the process described in Example 1, Step b, starting from the compound described in the preceding Step.

Melting point: 216–218° C.

EXAMPLE 19

2-(4,5-Dihydro-1H-2-imidazolyl)-6-methoxy-4-methyl-3,4-dihydro-2H-1,4-benzoxazine Oxalate

Step a: 2-Ethoxycarbonyl-6-methoxy-4-methyl-3,4-dihydro-2H-1,4-benzoxazine

The expected product is obtained in accordance with the process described in Example 1, Step a, replacing iodopropane by iodomethane and using as starting material 2-ethoxycarbonyl-6-methoxy-2,3-dihydro-2H-1,4-benzoxazine, prepared in accordance with the method described in J. Heterocyclic Chem., 1985, 22, 177, starting from 2-amino-4-methoxyphenol (described in J. Org. Chem., 1996, 3289).

Step b: 2-(4,5-Dihydro-1H-2-imidazolyl)-6-methoxy-4-methyl-3,4-dihydro-2H-1,4-benzoxazine Oxalate The expected product is obtained in accordance with the process described in Example 1, Step b, starting from the compound described in the preceding Step.

Melting point: 202–204° C.

EXAMPLE 20

2-(4,5-Dihydro-1H-2-imidazolyl)-6-fluoro-4-methyl-3,4-dihydro-2H-1,4-benzoxazine Oxalate

Step a: 2-Ethoxycarbonyl-6-fluoro-4-methyl-3,4-dihydro-2H-1,4-benzoxazine

The expected product is obtained in accordance with the process described in Example 1, Step a, replacing iodopropane by iodomethane and using as starting material the 2-ethoxycarbonyl-6-fluoro-2,3-dihydro-2H-1,4-benzoxazine described in Preparation A.

Step b: 2-(4,5-Dihydro-1H-2-imidazolyl)-6-fluoro-4-methyl-3,4-dihydro-2H-1,4-benzoxazine Oxalate The expected product is obtained in accordance with the process described in Example 1, Step b, starting from the compound described in the preceding Step.

Melting point: 198–200° C.

EXAMPLE 21

2-(4,5-Dihydro-1H-2-imidazolyl)-6-hydroxy-4-methyl-3,4-dihydro-2H-1,4-benzoxazine Oxalate

1.14 mmol (0.11 ml) of boron tribromide are added to a solution of 0.57 mmol (140 mg) of the compound described in Example 19 in 5 ml of dichloromethane at −10° C. The reaction mixture is heated at reflux for 1 hour. The reaction mixture is hydrolysed and rendered alkaline by a 10% sodium hydroxide solution. After extraction with dichloromethane, the organic phases are combined, dried over magnesium sulphate and concentrated. Purification by chromatography on silica gel using a dichloromethane/triethylamine mixture (100/1) as eluant enables the expected product to be obtained. The corresponding oxalate is obtained by the action of a titrated solution of oxalic acid in ethanol.

EXAMPLE 22

2-(4,5-Dihydro-1H-2-imidazolyl)-4-methyl-6-trifluoromethyl-3,4-dihydro-2H-1,4-benzoxazine Oxalate

Step a: 2-Ethoxycarbonyl-4-methyl-6-trifluoromethyl-3,4-dihydro-2H-1,4-benzoxazine The expected product is obtained in accordance with the process described in Example 1, Step a, replacing iodopropane by iodomethane and using as starting material the 2-ethoxycarbonyl-6-trifluoromethyl-3,4-dihydro-2H-1,4-benzoxazine described in Preparation B.

Step b: 2-(4,5-Dihydro-1H-2-imidazolyl)-4-methyl-6-trifluoromethyl-3,4-dihydro-2H-1,4-benzoxazine Oxalate The expected product is obtained in accordance with the process described in Example 1, Step b, starting from the compound described in the preceding Step.

EXAMPLE 23

2-(4,5-Dihydro-1H-2-imidazolyl)-4-methyl-8-trifluoromethyl-3,4-dihydro-2H-1,4-benzoxazine oxalate

Step a: 2-Ethoxycarbonyl-4-methyl-8-trifluoromethyl-3,4-dihydro-2H-1,4-benzoxazine The expected product is obtained in accordance with the process described in Example 1, Step a, replacing iodopropane by iodomethane and using as starting material 2-ethoxycarbonyl-8-trifluoromethyl-3,4-dihydro-2H-1,4-benzoxazine described in Preparation C.

Step b: 2-(4,5-Dihydro-1H-2-imidazolyl)-4-methyl-8-trifluoromethyl-3,4-dihydro-2H-1,4-benzoxazine oxalate The expected product is obtained in accordance with the process described in Example 1, Step b, starting from the compound described in the preceding Step.

EXAMPLE 24

6-Acetyl-2-(4,5-dihydro-1H-2-imidazolyl)-4-methyl-3,4-dihydro-2H-1,4-benzoxazine oxalate

Step a: 6-Acetyl-2-ethoxycarbonyl-4-methyl-3,4-dihydro-2H-1,4-benzoxazine 1.6 mmol (0.1 ml) of acetyl chloride and 4 mmol (545 mg) of aluminum chloride are added to a solution of 1.6 mmol (355 mg) of 2-ethoxycarbonyl-4-methyl-3,4-dihydro-2H-1,4-benzoxazine (described in J. Heterocyclic Chem., 1985, 22, 177) in 18 ml of dichloromethane at −10° C. The reaction mixture is stirred at room temperature for 1 hour before being hydrolysed by a cooled aqueous solution of 2 M hydrochloric acid. The mixture is extracted with dichloromethane and the organic phase is washed with a saturated solution of $NaHCO_3$, dried over magnesium sulphate, concentrated and purified by chromatography on silica gel using a petroleum ether/ethyl acetate mixture (7/3) as eluant to yield the expected product.

Note: the compound 7-acetyl-2-ethoxycarbonyl-4-methyl-3,4-dihydro-2H-benzoxazine is also isolated.

Step b: 6-Acetyl-2-(4,5-dihydro-1H-2-imidazolyl)-4-methyl-3,4-dihydro-2H-1,4-benzoxazine oxalate The expected product is obtained in accordance with the process described in Example 1, Step b, starting from the compound described in the preceding Step.

EXAMPLE 25

7-Acetyl-2-(4,5-dihydro-1H-2-imidazolyl)-4-methyl-3,4-dihydro-2H-1,4-benzoxazine oxalate The expected product is obtained in accordance with the process described in Example 1, Step b, using as starting material the 7-acetyl-2-ethoxycarbonyl-4-methyl-3,4-dihydro-2H-1,4-benzoxazine isolated in Step a of Example 24.

EXAMPLE 26

2-(4,5-Dihydro-1H-2-imidazolyl)-6-formyl-4-methyl-3,4-dihydro-2H-1,4-benzoxazine oxalate Step a: 2-Ethoxycarbonyl-6-formyl-4-methyl-3,4-dihydro-2H-1,4-benzoxazine 6.5 mmol (0.6 ml) of dichloromethyl methyl ester and 6.5 mmol (0.7 ml) of titanium tetrachloride are added to a solution of 4.3 mmol (950 mg) of 2-ethoxycarbonyl-4-methyl-3,4-dihydro-2H-1,4-benzoxazine (described in J. Heterocyclic Chem., 1985, 22, 177) in 30 ml of dichloromethane at −10° C. Stirring is maintained at from −10° C. to 0° C. for 2 hours. The reaction mixture is hydrolysed using a water/ice mixture, and extracted with dichloromethane. The organic phase is dried over magnesium sulphate, concentrated and purified by chromatography on silica gel using a petroleum ether/ethyl acetate mixture (7/3) as eluant to yield the title product.

Note: the compound 2-ethoxycarbonyl-7-formyl-4-methyl-3,4-dihydro-2H-1,4-benzoxazine is also isolated.

Step b: 2-(4,5-Dihydro-1H-2-imidazolyl)-6-formyl-4-methyl-3,4-dihydro-2H-1,4-benzoxazine oxalate The expected product is obtained in accordance with the process described in Example 1, Step b, starting from the compound described in the preceding Step.

EXAMPLE 27

2-(4,5-Dihydro-1H-2-imidazolyl)-7-formyl-4-methyl-3,4-dihydro-2H-1,4-benzoxazine oxalate The expected product is obtained in accordance with the process described in Example 1, Step b, using as starting material the 2-ethoxycarbonyl-7-formyl-4-methyl-3,4-dihydro-2H-1,4-benzoxazine isolated in Step a of Example 26.

EXAMPLE 28

2-(4,5-Dihydro-1H-2-imidazolyl)-7-methoxy-4-methyl-3,4-dihydro-2H-1,4-benzoxazine oxalate Step a: 2-Ethoxycarbonyl-7-methoxy-4-methyl-3,4-dihydro-2H-1,4-benzoxazine The expected product is obtained in accordance with the process described in Example 1, Step a, replacing iodopropane by iodomethane and using as starting material the 2-ethoxycarbonyl-7-methoxy-3,4-dihydro-2H-1,4-benzoxazine described in Preparation D.

Step b: 2-(4,5-Dihydro-1H-2-imidazolyl)-7-methoxy-4-methyl-3,4-dihydro-2H-1,4-benzoxazine oxalate The expected product is obtained in accordance with the process described in Example 1, Step b, starting from the compound described in the preceding Step.

EXAMPLE 29

7-Chloro-2-(4,5-dihydro-1H-2-imidazolyl)-4-methyl-3,4-dihydro-2H-1,4-benzoxazine oxalate Step a: 7-Chloro-2-ethoxycarbonyl-4-methyl-3,4-dihydro-2H-1,4-benzoxazine The expected product is obtained in accordance with the process described in Example 1, Step a, replacing iodopropane by iodomethane and using as starting material 7-chloro-2-ethoxycarbonyl-3,4-dihydro-2H-1,4-benzoxazine (obtained in accordance with the process described in J. Heterocyclic Chem. 1985, 22, 177, starting from 5-chloro-2-hydroxyaniline).

Step b: 7-Chloro-2-(4,5-dihydro-1H-2-imidazolyl)-4-methyl-3,4-dihydro-2H,-1,4-benzoxazine oxalate The expected product is obtained in accordance with the process described in Example 1, Step b, starting from the compound described in the preceding Step.

EXAMPLE 30

2-(4,5-Dihydro-1H-2-imidazolyl)-4-methyl-3,4,6,7,8,9-hexahydro-2H-naphtho[2,3-b][1,4]oxazine oxalate

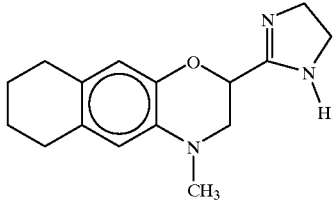

Step a: 2-Ethoxycarbonyl-4-methyl-3,4,6,7,8,9-hexahydro-2H-naphtho-[2,3-b][1,4]oxazine The expected product is obtained in accordance with the process described in Example 1, Step a, replacing iodopropane by iodomethane and using as starting material 2-ethoxycarbonyl-3,4,6,7,8,9-hexahydro-2H-naphtho[2,3-b][1,4]oxazine, prepared in accordance with the process described in J. Heterocyclic Chem., 1985, 22, 177, starting from 3-amino-5,6,7,8-tetrahydro-2-naphthol (described in Chem. Pharm. Bull., 1991, 39, 2896).

Step b: 2-(4,5-Dihydro-1H-2-imidazolyl)-4-methyl-3,4,6,7,8,9-hexahydro-2H-naphtho[2,3-b][1,4]oxazine oxalate The expected product is obtained in accordance with the process described in Example 1, Step b, starting from the compound described in the preceding Step.

Melting point (base): 120–122° C.

EXAMPLE 31

2-(4,5-Dihydro-1H-2-imidazolyl)-4-methyl-3,4-dihydro-2H-naphtho[1,2-b][1,4]oxazine oxalate

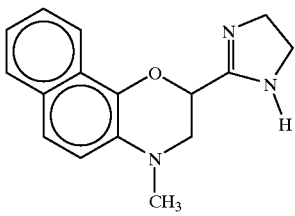

Step a: 2-Ethoxycarbonyl-4-methyl-3,4-dihydro-2H-naphtho[1,2-b][1,4]oxazine

The expected product is obtained in accordance with the process described in Example 1, Step a, replacing iodopropane by iodomethane and using as starting material 2-ethoxycarbonyl-3,4-dihydro-2H-naphtho[1,2-b][1,4]oxazine, prepared in accordance with the process described in J. Heterocyclic Chem., 1985, 22, 177, starting from 2-amino-1-naphthol.

Step b: 2-(4,5-Dihydro-1H-2-imidazolyl)-4-methyl-3,4-dihydro-2H-naphtho[1,2-b][1,4]oxazine oxalate The expected product is obtained in accordance with the process described in Example 1, Step b, starting from the compound described in the preceding Step.

Melting point: >260° C.

EXAMPLE 32

4-Cyclobutyl-2-(4,5-dihydro-1H-2-imidazolyl)-6-methyl-3,4-dihydro-2H-1,4-benzoxazine oxalate The expected product is obtained in accordance with the process described in Example 2, replacing iodopropane by cyclobutyl chloride in Step a.

EXAMPLE 33

4-Cyclopropylmethyl-2-(4,5-dihydro-1H-2-imidazolyl)-6-methyl-3,4-dihydro-2H-1,4-benzoxazine oxalate The expected product is obtained in accordance with the process described in Example 2, replacing iodopropane by bromomethylcyclopropane in Step a.

EXAMPLE 34

4-Benzyl-2-(4,5-dihydro-1H-2-imidazolyl)-6-methyl-3,4-dihydro-2H-1,4-benzoxazine oxalate The expected product is obtained in accordance with the process described in Example 2, replacing iodopropane by benzyl bromide in Step a.

EXAMPLE 35

2-Allyl-2-(4,5-dihydro-1H-2-imidazolyl)-4,6-dimethyl-3,4-dihydro-2H-1,4-benzoxazine oxalate The expected product is obtained in accordance with the process described in Example 5, replacing iodomethane by allyl bromide in Step a.

EXAMPLE 36

2-(4,5-Dihydro-1H-2-imidazolyl)-4,6-dimethyl-2-propyl-3,4-dihydro-2H-1,4-benzoxazine oxalate The expected product is obtained in accordance with the process described in Example 5, replacing iodomethane by iodopropane in Step a.

EXAMPLE 37

2-Bromo-2-(4,5-dihydro-1H-2-imidazolyl)-4,6-dimethyl-3,4-dihydro-2H-1,4-benzoxazine oxalate Step a: 2-Bromo-2-ethoxycarbonyl-4,6-dimethyl-3,4-dihydro-2H-1,4-benzoxazine 3.1 mmol (570 mg) of N-bromosuccinimide and 50 mg of benzoyl peroxide are added to a solution of 3.1 mmol (730 mg) of the compound described in Step a of Example 2 in 15 ml of carbon tetrachloride. The reaction mixture is heated at reflux for 5 hours. After cooling, the precipitate is filtered off, and the filtrate is concentrated and purified by chromatography on silica gel to yield the expected compound.

Step b: 2-Bromo-2-(4,5-dihydro-1H-2-imidazolyl)-4,6-dimethyl-3,4-dihydro-2H-1,4-benzoxazine oxalate The expected product is obtained in accordance with the process described in Example 1, Step b, starting from the compound described in the preceding Step.

EXAMPLE 38

2-(4,5-Dihydro-1H-2-imidazolyl)-2-methoxy-4,6-dimethyl-3,4-dihydro-2H-1,4-benzoxazine oxalate Step a: 2-Ethoxycarbonyl-2-methoxy-4-methyl-3,4-dihydro-2H-1,4-benzoxazine 2.5 mmol of ethylenediamine are added to a solution of 2.1 mmol of the compound described in Step a of Example 37 in 8 ml of methanol at 0° C. The reaction mixture is stirred for 18 hours at room temperature and then hydrolysed by a saturated $NaHCO_3$ solution. After extraction with dichloromethane, the combined organic phases are dried over magnesium sulphate and concentrated. The resulting residue is purified by chromatography on silica gel using dichloromethane as eluant to yield the expected compound.

Step b: 2-(4,5-Dihydro-1H-2-imidazolyl)-2-methoxy-4,6-dimethyl-3,4-dihydro-2H-1,4-benzoxazine oxalate The expected product is obtained in accordance with the process described in Example 1, Step b, starting from the compound described in the preceding Step.

EXAMPLE 39

2-Benzyloxy-2-(4,5-dihydro-1H-2-imidazolyl)-4,6-dimethyl-3,4-dihydro-2H-1,4-benzoxazine oxalate The expected product is obtained in accordance with the process described in Example 38, replacing methanol by benzyl alcohol in Step a.

EXAMPLE 40

2-(4,5-Dihydro-1H-2-imidazolyl)-4,6-dimethyl-4H-1,4-benzoxazine oxalate

Step a: 4,6-Dimethyl-2-ethoxycarbonyl-4H-1,4-benzoxazine

The expected product is obtained in accordance with the process described in Tetrahedron Lett., 1978, 1059, using the compound described in Example 2, Step a, as starting material.

Step b: 2-(4,5-Dihydro-1H-2-imidazolyl)-4,6-dimethyl-4H-1,4-benzoxazine oxalate

The expected product is obtained in accordance with the process described in Example 1, Step b, starting from the compound described in the preceding Step.

The compounds of Examples 41 to 44 are obtained in accordance with the process described in Example 40, using as starting material the 3,4-dihydro-2H-1,4-benzoxazines described in the preceding Examples.

EXAMPLE 41

6-Chloro-2-(4,5-dihydro-1H-2-imidazolyl)-4-methyl-4H-1,4-benzoxazine oxalate

EXAMPLE 42

2-(4,5-Dihydro-1H-2-imidazolyl)-4,7-dimethyl-4H-1,4-benzoxazine oxalate

EXAMPLE 43

2-(4,5-Dihydro-1H-2-imidazolyl)-5,6-dihydro[1,4]oxazino[2,3,4-h,i]indole oxalate

EXAMPLE 44

2-(4,5-Dihydro-1H-2-imidazolyl)-4-methyl-6-trifluoromethyl-4-H-1,4-benzoxazine oxalate The compounds of Examples 45 to 60 are obtained using processes identical to those described in the preceding Examples, starting from substrates having a 2-ethoxycarbonyl-3,4-dihydro-2H-1,4-benzothiazine structure (J. Heterocyclic Chem., 1985, 177, 22; ibid., 1980, 17, 377).

EXAMPLE 45

2-(4,5-Dihydro-1H-2-imidazolyl)-4,6-dimethyl-3,4-dihydro-2H-1,4-benzothiazine oxalate

EXAMPLE 46

6-Chloro-2-(4,5-dihydro-1H-2-imidazolyl)-4-methyl-3,4-dihydro-2H-1,4-benzothiazine oxalate

EXAMPLE 47

2-(4,5-Dihydro-1H-2-imidazolyl)-4-methyl-6-trifluoromethyl-3,4-dihydro-2H-1,4-benzothiazine oxalate

EXAMPLE 48

2-(4,5-Dihydro-1H-2-imidazolyl)-6-methoxy-4-methyl-3,4-dihydro-2H-1,4-benzothiazine oxalate

EXAMPLE 49

6-Acetyl-(4,5-Dihydro-1H-2-imidazolyl)-4-methyl-3,4-dihydro-2H-1,4-benzothiazine oxalate

EXAMPLE 50

2-(4,5-Dihydro-1H-2-imidazolyl)-4,7-dimethyl-3,4-dihydro-2H-1,4-benzothiazine oxalate

EXAMPLE 51

7-Chloro-2-(4,5-dihydro-1H-2-imidazolyl)-4-methyl-3,4-dihydro-2H-1,4-benzothiazine oxalate

EXAMPLE 52

2-(4,5-Dihydro-1H-2-imidazolyl)-4-methyl-8-trifluoromethyl-3,4-dihydro-2H-1,4-benzothiazine oxalate

EXAMPLE 53

4-Cyclopropylmethyl-2-(4,5-dihydro-1H-2-imidazolyl)-6-methyl-3,4-dihydro-2H-1,4-benzothiazine oxalate

EXAMPLE 54

4-Benzyl-2-(4,5-dihydro-1H-2-imidazolyl)-6-methyl-3,4-dihydro-2H-1,4-benzothiazine oxalate

EXAMPLE 55

6-Chloro-2-(4,5-dihydro-1H-2-imidazolyl)-2,4-dimethyl-3,4-dihydro-2H-1,4-benzothiazine oxalate

EXAMPLE 56

2-(4,5-Dihydro-1H-2-imidazolyl)-4,6-dimethyl-2-propyl-3,4-dihydro-2H-1,4-benzothiazine oxalate

EXAMPLE 57

2-(4,5-Dihydro-1H-2-imidazolyl)-2,3,5,6-tetrahydro[1,4]thiazino[2,3,4-h,i]indole oxalate

EXAMPLE 58

2-(4,5-Dihydro-1H-2-imidazolyl)-2,3,6,7-tetrahydro-5H[1,6]thiazino[2,3,4-i,j]quinoline oxalate

EXAMPLE 59

2-(4,5-Dihydro-1H-2-imidazolyl)-4,6-dimethyl-4H-1,4-benzothiazine oxalate

EXAMPLE 60

2-(4,5-Dihydro-1H-2-imidazolyl)-4,7-dimethyl-4H-1,4-benzothiazine oxalate

The compounds of Examples 61 to 66 are obtained using processes identical to those described in Examples 1 to 44, starting from substrates having a 2-ethoxycarbonyl-1,2,3,4-tetrahydroquinoline structure (Khim. Geterotsikl. Soedin., 1988, (1), 77).

EXAMPLE 61

3-(4,5-Dihydro-1H-2-imidazolyl)-1-methyl-1,2,3,4-tetrahydroquinoline oxalate

EXAMPLE 62

3-(4,5-Dihydro-1H-2-imidazolyl)-1-propyl-1,2,3,4-tetrahydroquinoline oxalate

EXAMPLE 63

1-Cyclopropylmethyl-3-(4,5-dihydro-1H-2-imidazolyl)-1,2,3,4-tetrahydroquinoline oxalate

EXAMPLE 64

3-(4,5-Dihydro-1H-2-imidazolyl)-1-methyl-3-propyl-1,2,3,4-tetrahydro-quinoline oxalate

EXAMPLE 65

7-Chloro-3-(4,5-dihydro-1H-2-imidazolyl-1-methyl-1,2,3,4-tetrahydro-quinoline oxalate

EXAMPLE 66

3-(4,5-Dihydro-1H-2-imidazolyl)-7-methoxy-1-methyl-1,2,3,4-tetrahydro-quinoline oxalate

EXAMPLE 67

2-(4,5-Dihydro-1H-2-imidazolylmethyl)-4,6-dimethyl-3,4-dihydro-2H-1,4-benzoxazine oxalate Step a: 4,6-Dimethyl-2-hydroxymethyl-3,4-dihydro-2H-1,4-benzoxazine 20 mmol of the compound described in Step a of Example 2 in 15 ml of tetrahydrofuran are added dropwise to a suspension of 40 mmol of lithium aluminium hydride in 100 ml of tetrahydrofuran at 0° C. The reaction is stirred at room temperature for 1 hour. After hydrolysis, the solution is filtered over Celite and the filtrate is concentrated. The residue is taken up in water and extracted with dichloromethane. The organic phase is dried over magnesium sulphate, concentrated and purified by chromatography on silica gel using a dichloromethane/methanol mixture (98/2) as eluant to yield the expected product.

Step b: 4,6-Dimethyl-2-iodomethyl-3,4-dihydro-2H-1,4-benzoxazine 13.4 mmol of triphenylphosphine and 27.4 mmol of imidazole are added to a solution of 6.1 mmol of the compound described in the preceding Step in 20 ml of toluene and 10 ml of acetonitrile. The mixture is brought to reflux and then 12.8 mmol of iodine are added. The reaction mixture is stirred at reflux for 1 hour. After cooling, the solvent is evaporated off, and the residue is hydrolysed and then extracted with dichloromethane. The organic phase is dried over magnesium sulphate, concentrated and purified by chromatography on silica gel using a petroleum ether/dichloromethane mixture (5/5) as eluant to yield the expected compound.

Step c: (4,6-Dimethyl-3,4-dihydro-2H-1,4-benzoxazin-2-yl)acetonitrile 28 mmol of potassium cyanide are added to a solution of 4 mmol of the compound described in the preceding Step in 6 ml of DMSO. The reaction mixture is stirred at room temperature for 36 hours. The mixture is then diluted with dichloromethane and washed 10 times with water. The organic phase is dried over magnesium sulphate, concentrated and purified by chromatography on silica gel using a dichloromethane/petroleum ether mixture (5/5) as eluant to yield the expected compound.

Step d: Ethyl 2-(4,6-dimethyl-3,4-dihydro-2H-1,4-benzoxazine-2-yl)acetate

The compound described in the preceding Step dissolved in a 10% sodium hydroxide solution is heated at reflux for 50 minutes. After cooling, the mixture is acidified by a 2 N hydrochloric acid solution and extracted with dichloromethane. The organic phase is dried over magnesium sulphate and concentrated. The residue is dissolved in ethanol in the presence of a catalytic quantity of para-toluenesulphonic acid. The reaction mixture is heated at reflux for 18 hours. After cooling, the solvent is evaporated off, and the residue is taken up in an ethyl acetate/water mixture and extracted. The organic phase is dried, concentrated and purified by chromatography on silica gel using a petroleum ether/ethyl acetate mixture (7/8) as eluant to yield the expected product.

Step e: 2-(4,5-Dihydro-1H-2-imidazolylmethyl)-4,6-dimethyl-3,4-dihydro-2H-1,4-benzoxazine oxalate The expected product is obtained in accordance with the process described in Example 1, Step b, starting from the compound described in the preceding Step.

The compounds of Examples 68 to 75 are obtained in accordance with a process identical to that described in Example 67 using as substrate the appropriate compounds described in Examples 1 to 66.

EXAMPLE 68

2-(4,5-Dihydro-1H-2-imidazolylmethyl)-2,4-dimethyl-3,4-dihydro-2H-1,4-benzoxazine oxalate

EXAMPLE 69

2-(4,5-Dihydro-1H-2-imidazolylmethyl)-4-methyl-6-trifluoromethyl-3,4-dihydro-2H-1,4-benzoxazine oxalate

EXAMPLE 70

4-Cyclopropylmethyl-2-(4,5-dihydro-1H-2-imidazolylmethyl)-6-methyl-3,4-dihydro-2H-1,4-benzoxazine oxalate

EXAMPLE 71

2-(4,5-Dihydro-1H-2-imidazolylmethyl)-4,6-dimethyl-3,4-dihydro-2H-1,4-benzothiazine oxalate

EXAMPLE 72

2-(4,5-Dihydro-1H-2-imidazolylmethyl)-6-methoxy-4-methyl-3,4-dihydro-2H-1,4-benzothiazine oxalate

EXAMPLE 73

2-(4,5-Dihydro-1H-2-imidazolylmethyl)-4,6-dimethyl-2-propyl-3,4-dihydro-2H-1,4-benzothiazine oxalate

EXAMPLE 74

3-(4,5-Dihydro-1H-2-imidazolylmethyl)-1-methyl-1,2,3,4-tetrahydroquinoline oxalate

EXAMPLE 75

3-(4,5-Dihydro-1H-2-imidazolylmethyl)-7-methoxy-1-methyl-1,2,3,4-tetrahydroquinoline oxalate

PHARMACOLOGICAL STUDY OF THE COMPOUNDS OF THE INVENTION

EXAMPLE A

Measurement of In Vitro Affinity for the $I_1$ and $I_2$ Receptors

The profile of binding to the imidazoline $I_1$ and $I_2$ receptors was determined for the compounds of the invention by evaluating the ability of those compounds to displace specific radioligands of the receptors in question.

The following Table indicates the radioligand used to label each receptor, the compound and the concentration selected to determine the non-specific fraction, and the tissue selected.

| Receptor or site | Radioligand | Non-specific | Tissue |
|---|---|---|---|
| $I_1$ | [$^3$H] clonidine + 10 μM noradrenaline | $10^{-5}$ M clonidine | bovine lateral reticulated nucleus |
| $I_2$ | [$^3$H] idazoxan + 10 μM noradrenaline | $10^{-5}$ M idazoxan | renal cortex of rabbit |

Results

The results obtained show the compounds of the invention to have a very high affinity for the $I_1$ and $I_2$ receptors, ranging from a few nanomoles to several tens of nanomoles.

By way of example, the compound of Example 2 has Ki values of $2.2 \times 10^{-8}$ M and $2.0 \times 10^{-9}$ M for the $I_1$ and $I_2$ receptors, respectively.

EXAMPLE B

Demonstration of Antihypertensive Activity in Anaesthetised Rats

The tests were carried out in 18-week-old male SHR rats. The rats are anaesthetised with pentobarbital (50 mg/kg i.p.). A catheter is introduced into the left carotid artery so as to record the systolic and diastolic arterial pressure and the heart rate. Only animals whose arterial pressure is higher than or equal to 170 mmHg are included in the study.

The parameters to be measured are allowed to stabilise for a period of at least 30 minutes.

The test compound, or carrier, is administered intraperitoneally at a dose of 25 mg/kg (the compound is suspended in distilled water containing 0.5% carboxymethylcellulose, the volume injected being 0.25 ml/100 g); the control animals are given only the carrier.

The measurements taken are expressed in mmHg for the arterial pressure and in bpm for the heart rate, and are compared with the base values.

A compound is considered to be active if the effect recorded on the arterial pressure or on the heart rate is greater than 25 mmHg or 50 bpm, respectively.

Results

The compounds of the invention appear to be able to lower the arterial pressure and the heart rate significantly.

EXAMPLE C

Demonstration of Hypotensive Activity in Anaesthetised Rabbits having Normal Blood Pressure The tests were carried out in male rabbits having normal blood pressure. The rabbits are anaesthetised with pentobarbital (40 mg/kg; i.v.), artificially ventilated and then curarised. The arterial pressure and the heart rate are measured using a catheter introduced into the right femoral artery.

Before each test, an equal volume of carrier is administered, and the parameters to be measured are allowed to stabilise. The test compound or the carrier is then administered, either intracisternally or intravenously, in increasing and cumulative doses of from 1 to 300 μg/kg.

The measurements of the instantaneous systolic and diastolic arterial pressure and of the heart rate are carried out from 5 to 10 minutes after the injections.

Results

The results are expressed as a variation percentage relative to the base values.

The compounds of the invention appear to lower the arterial pressure and heart rate significantly with a dose-dependent effect.

By way of example, the compound of Example 2 induces a drop of from 19 to 30% in the arterial pressure and of from 9 to 22% in the heart rate.

EXAMPLE D

Demonstration of Antihypertensive Activity in Conscious Rats

The tests were carried out in SHR rats. The animals are anaesthetised. A heparinised catheter is introduced into the left carotid artery and connected to a recording apparatus so as to measure the systolic and diastolic arterial pressure and the heart rate. The animals are returned to their cage and the tests are carried out after 24 hours.

The parameters to be measured stabilise during a period of at least 30 minutes, during which a maximum of 1.5 ml of saline solution is injected in such a manner as to optimise the measurements. Only animals whose arterial pressure is higher than or equal to 170 mmHg are included in the study.

The test compounds of the carrier are administered orally and the measurements are carried out before the treatment and every ten minutes after treatment, for 4 hours, and then 8 and 24 hours after treatment.

Results

The compounds of the invention appear to be able to lower the arterial pressure and the heart rate significantly.

By way of example, the compound of Example 2 given at a dose of 15 mg/kg allowed the arterial pressure to be normalized.

EXAMPLE E

Acute Toxicity

Acute toxicity was evaluates after oral administration of a dose of 650 mg.kg$^{-1}$ to groups each comprising 8 mice (26±2 grammes). The animals were observed at regular intervals during the course of the first day and daily for the two weeks following treatment.

Most of the compounds of the invention appear to be totally atoxic. Most of them bring about no deaths after administration of a dose of 650 mg/kg$^{-1}$ and, generally, no disorders are observed after administration of that dose.

EXAMPLE F

Pharmaceutical Composition

Formulation for the preparation of 1000 tablets each containing 10 mg of active ingredient.

| | |
|---|---|
| Compound of Example 2 | 10 g |
| Hydroxypropyl cellulose | 2 g |
| Wheat starch | 10 g |
| Corn starch | 10 g |
| Lactose | 100 g |
| Magnesium stearate | 3 g |
| Talc | 3 g |

We claim:

1. A compound selected from those of formula (I):

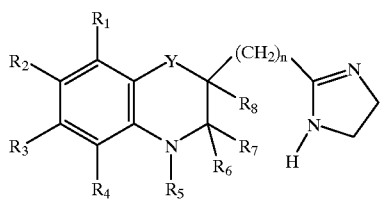

(I)

wherein:

n is 0 or 1,

Y represents oxygen, sulphur, or $CH_2$;

$R_1$, $R_2$, $R_3$ and $R_4$, which may be identical or different, each represent hydrogen, halogen, ($C_3$–$C_7$)cycloalkyl, linear or branched ($C_1$–$C_6$)alkoxy, hydroxy, linear or branched ($C_1$–$C_6$)hydroxyalkyl, linear or branched ($C_1$–$C_6$)trihaloalkyl, linear or branched ($C_1$–$C_6$)alkylcarbonyl, formyl, cyano, carboxy, linear or branched ($C_1$–$C_6$)alkoxy-carbonyl, nitro, or optionally-substituted amino, or, ($R_1$–$R_2$) or ($R_2$–$R_3$) or ($R_3$–$R_4$) form with the carbon atoms bearing them an optionally-substituted saturated or unsaturated 5- or 6-member ring, at most three of $R_1$, $R_2$, $R_3$, and $R_4$ representing hydrogen, $R_5$ represents hydrogen, ($C_3$–$C_7$)cycloalkyl or linear or branched ($C_1$–$C_6$)alkyl optionally substituted by a $C_3$–$C_7$)cycloalkyl group, and optionally substituted phenyl, or, with $R_4$, forms a saturated or unsaturated 5-, 6-, or 7-member ring optionally substituted by one or more identical or different groups selected from: linear or branched ($C_1$–$C_6$)alkyl, linear or branched ($C_1$–$C_6$)alkoxy, hydroxy, oxo, and optionally-substituted amino, $R_6$ and $R_7$ each represent hydrogen, or together form an oxo group, $R_8$ represents halogen, hydrogen, linear or branched ($C_1$–$C_6$)alkyl, linear or branched ($C_1$–$C_6$)alkenyl, hydroxy, linear or branched ($C_1$–$C_6$)alkoxy optionally substituted by amino, pyrrolyl or piperidinyl, ($C_3$–$C_7$) cycloalkyloxy, optionally-substituted phenyloxy, or optionally-substituted benzyloxy;

or, with $R_7$, forms a bond, their N-oxides, their enantiomers and diastereoisomers, and addition salts thereof with a pharmaceutically-acceptable acid or base.

2. A compound of claim 1 wherein n is 0, their N-oxides, their enantiomers and diastereoisomers, and addition salts thereof with a pharmaceutically-acceptable acid or base.

3. A compound of claim 1 wherein Y represents oxygen, their N-oxides, their enantiomers and diastereoisomers, and addition salts thereof with a pharmaceutically-acceptable acid or base.

4. A compound of claim 1 wherein Y represents sulphur, their N-oxides, their enantiomers and diastereoisomers, and addition salts thereof with a pharmaceutically-acceptable acid or base.

5. A compound of claim 1 wherein each of $R_6$, $R_7$ and $R_8$ represents hydrogen, their N-oxides, their enantiomers and diastereoisomers, and addition salts thereof with a pharmaceutically-acceptable acid.

6. A compound of claim 1 wherein $R_5$ represents linear or branched ($C_1$–$C_6$)alkyl, their N-oxides, their enantiomers and diastereoisomers, and addition salts thereof with a pharmaceutically-acceptable acid.

7. A compound of claim 1 wherein three of the groups $R_1$, $R_2$, $R_3$ and $R_4$ are identical and each of the three represents hydrogen, the remaining group being as defined in claim 1, their N-oxides, their enantiomers and diastereoisomers, and addition salts thereof with a pharmaceutically, acceptable acid.

8. A compound of claim 1 wherein ($R_1$–$R_2$) or ($R_2$–$R_3$) or ($R_3$–$R_4$) form with the carbon atoms bearing them an optionally-substituted saturated or unsaturated 5- or 6-member ring, their N-oxides, their enantiomers and diastereoisomers, and addition salts thereof with a pharmaceutically-acceptable acid.

9. A compound of claim 1, wherein $R_4$ and $R_5$ together form a saturated or unsaturated 5-, 6-, or 7-member ring optionally substituted by one or more groups selected from: linear or branched ($C_1$–$C_6$) alkyl, linear or branched ($C_1$–$C_6$) alkoxy, hydroxy, oxo, and optionally substituted amino, their N-oxides, their enantiomers and diastereoisomers, and addition salts thereof with a pharmaceutically-acceptable acid or base.

10. A compound of claim 1 wherein Y represents oxygen, n is 0, each of $R_6$, $R_7$ and $R_8$ represents hydrogen each of $R_1$, $R_2$, $R_3$ and $R_4$, which may be identical or different, are selected from hydrogen, halogen ($C_3$–$C_7$)cycloalkyl, linear or branched ($C_1$–$C_6$)alkoxy, hydroxy, linear or branched ($C_1$–$C_6$) hydroxyalkyl, linear or branched ($C_1$–$C_6$) trihaloalkyl, linear or branched ($C_1$–$C_6$)alkyl-carbonyl, formyl, cyano, carboxy, linear or branched ($C_1$–$C_6$)alkoxy-carbonyl, nitro, or optionally substituted amino or ($R_1$–$R_2$) or ($R_2$–$R_3$) or ($R_3$–$R_4$) form with the carbon atoms bearing them an optionally-substituted saturated or unsaturated 5- or 6-member ring, whilst $R_5$ represents linear or branched ($C_1$–$C_6$)alkyl or, with $R_4$, forms a saturated or unsaturated 5-, 6-, or 7-member ring, their N-oxides, their enantiomers and diastereoisomers, and addition salts thereof with a pharmaceutically-acceptable acid or base.

11. A compound of claim 1 which is selected from the group consisting of 6-chloro-2-(4,5-dihydro-1H-2-imidazolyl)-4-methyl-3,4-dihydro-2H-1,4-benzoxazine, its N-oxides, enantiomers and diastereoisomers, and addition salts thereof with a pharmaceutically-acceptable acid.

12. A compound of claim 1 which is selected from the group consisting of:

2-(4,5-dihydro-1H-2-imidazolyl)-2,3,5,6-tetrahydro[1,4]oxazino[2,3,4-h,i]indole, 2-(4,5-dihydro-1H-2-imidazolyl)-2,3-dihydro[1,4]oxazino[2,3,4-h,i]indole, their N-oxides, their enantiomers and diastereoisomers, and addition salts thereof with a pharmaceutically-acceptable acid.

13. A method for treating a living body afflicted with a condition requiring an imidazoline receptors ligand, selected from cardiovascular diseases and arterial hypertension, diabetes, obesity, and psychiatric or neurological disorders, selected from depression, Parkinson's disease, anorexia, or Alzheimer's disease, comprising the step of administering to the living body an amount of a compound of claim 1 which is effective for alleviation of said condition.

14. A method for treating a living body afflicted with a condition selected from cardiovascular disease and arterial hypertension, comprising the step of administering to the living body an amount of a compound of claim 1 which is effective for alleviation of said condition.

15. A pharmaceutical composition useful as an imidazoline receptors ligand comprising as active principle an effective amount of a compound as claimed in claim 1, together with one or more pharmaceutically-acceptable excipients or vehicles.

16. A compound of claim 1 which is selected from the group consisting of 2-(4,5-dihydro-1H-2-imidazolyl)-6-fluoro-4-methyl-3,4-dihydro-2H-1,4-benzoxazine, its N-oxides, enantiomers and diastereoisomers, and addition salts thereof with a pharmaceutically-acceptable acid.

* * * * *

UNITED STATES PATENT AND TRADEMARK OFFICE
CERTIFICATE OF CORRECTION

PATENT NO.   : 6,057,317
DATED        : May 2, 2000
INVENTOR(S)  : G. Guillaumet, J.Y. Merour, F. Touzeau, B. Pfeiffer, P. Renard, E. Scalbert It is certified that error appears in the above-identified patent and that said Letters Patent is hereby corrected as shown below:

Column 1,
Line 28, "retroventral" should read: -- rostroventral --.

Column 3,
Line 35, insert a -- , -- (comma) after the "0".
Line 36, insert -- a -- between "represents" and "hydrogen".

Column 4,
Line 23, "a defined" should read -- as defined --.

Column 5,
Line 38 (approx.), "c" at the end of the line should read -- a --.

Column 7,
Line 15, insert the word -- as -- between "are" and "defined".
Line 45, between "R'$_8$," and "G$_1$" insert -- R$_9$ --.

Column 11,
Line 5, "-2H1,4 -" should read -- -2H-1,4- --.
Line 64 (approx), "-imidiazolyl) -" should read -- -imidazolyl) -".

Column 27,
Line 27, "-4-H-" should read: -- -4H- --.

Column 34,
Line 47, change the "comma" after "pharmaceutically" to a -- - -- (hyphen).

Signed and Sealed this

Twenty-third Day of October, 2001

*Attest:*

NICHOLAS P. GODICI
*Attesting Officer*   Acting Director of the United States Patent and Trademark Office